(12) United States Patent
Okada et al.

(10) Patent No.: US 7,763,708 B2
(45) Date of Patent: Jul. 27, 2010

(54) METHODS AND COMPOSITIONS FOR MODULATING C5-A-MEDIATED INFLAMMATORY RESPONSES

(75) Inventors: Hidechika Okada, Nagoya (JP); Noriko Okada, Nagoya (JP)

(73) Assignee: Institute for Protein Science Co., Ltd., Aichi (JP)

( * ) Notice: Subject to any disclaimer, the term of this patent is extended or adjusted under 35 U.S.C. 154(b) by 1024 days.

(21) Appl. No.: 11/202,449

(22) Filed: Aug. 11, 2005

(65) Prior Publication Data

US 2006/0063701 A1    Mar. 23, 2006

Related U.S. Application Data

(60) Provisional application No. 60/601,038, filed on Aug. 12, 2004.

(51) Int. Cl.
*A61K 38/10* (2006.01)
(52) U.S. Cl. ............................. 530/326; 530/324; 514/2
(58) Field of Classification Search ..................... 514/2; 530/326, 324
See application file for complete search history.

(56) References Cited

U.S. PATENT DOCUMENTS

| | | | | |
|---|---|---|---|---|
| 5,677,195 A | * | 10/1997 | Winkler et al. | 436/518 |
| 5,885,837 A | * | 3/1999 | Winkler et al. | 506/9 |
| 5,902,723 A | * | 5/1999 | Dower et al. | 435/6 |
| 6,027,880 A | * | 2/2000 | Cronin et al. | 435/6 |
| 6,040,193 A | * | 3/2000 | Winkler et al. | 506/16 |
| 6,124,102 A | * | 9/2000 | Fodor et al. | 506/9 |

OTHER PUBLICATIONS

Fujita, Emiko (Journal of Immunology 172(10), 6382-6387, 2004).*
Baranyi (J. Immunol 157, 4591-4601, 1996).*
Baranyi, et al (1996), "Antisense Homology Boxes in C5a Receptor And C5a Anaphylatoxin". J. Immun. 1996, 157:4591-4601.
Campbell, et al (2002), "A Novel Genetic Algorithm For Designing Mimetic Peptides That Interfere With The Function Of A Target Molecule". Microbiol.Immun. 2002, 46(3), 211-215.
Czermak, et al (1999), "Protective Effects of C5a Blockade In Sepsis". Nature Medicine, vol. 5, No. 7 (788-792).
Fodor, et al (1991), "Light-Directed, Spatially Addressable Parallel Chemical Syntheses" Science, vol. 251 (767-773), Feb. 1991.
Gerard, et al (1994), "C5a Anaphylatoxin And Its Seven Transmembrane-Segment Receptor." Ann. Rev. Immunol. 1994. 12:775-808.
Godowski, et al (1988), "Signal Transduction And Transcriptional Regulation By Glucocorticoid Receptor-LexA Fusion Proteins." Science, Voll. 241 (812-817), Aug. 1988.
Hruby, et al (1990), "Emerging Approaches In The Molecular Design Of Receptor-Selective Peptide Ligands: Conformational, Topographical And Dynamic Considerations". Biochem. J. (1990) 268,249-262.

Kawai, et al (1991), "Identification And Syntheses Of A Receptor Binding Site In Human Anaphylatoxin C5a". J. Med. Chem. 1991, 34, 2068-2071.
Kondo, et al, (2001) "The Role of C5a In The Development Of Thrombotic Glomerulonephritis In Rats". Clin. Exp. Immunol. 2001; 124:323-329.
Konteatis, et al, (1994) "Development of C5a Receptor Antagonists". J.Immunol. 1994, 153:4200.
Matsuo, et al, (1994) "In Vivo Effects Of Monoclonal Antibodies That Functionally Inhibit Complement Regulatory Proteins in Rats." J. Exp. Med. 1994, 180:1619-1627.
Mizuno, et al (1999) "Inhibition Of A Membrane Complement Regulatory Protein By A Monoclonal Antibody Induces Acute Lethal Shock In Rats Primed With Lipopolysaccharide." J. Immunol. 1999, 162:5477-5482.
Mollison, et al (1989), "Identification Of Receptor-Binding Residues In The Inflammatory Complement Protein C5a By Site-Directed Mutagenesis." Proc. Natl. Acad. Sci.—Immunology (Jan. 1989) 86:292-296.
Owicki, et al (1990), "Continuous Monitoring Of Receptor-Mediated Changes In The Metabolic Rates Of Living Cells." Proc. Natl. Acad. Sci.—Chemistry (May 1990) 87:4077-4011.
Parce, et al (1989), "Detection Of Cell-Affecting Agents With A Silicon Bisensor." Science (Oct. 13, 1989) 246:243-247.
Pellas, et al (1998), "Novel C5a Receptor Antagonists Regulate Neutrophil Functions in Vitro and in Vivo." J. Immunol. 1998, 160:5626-5621.
Shimomura, et al (2003), "Modulation Of Procarboxypeptidase R (ProCPR) Activation By Complementary Peptides To Thrombolodulin." Microbiol. Immunol. 47(3), 241-245, 2003.
Stevens, et al (1986), "Effects of Anti-C5a Antibodies On The Adult Respiratory Distress Syndrome In Septic Primates." J. Clin. Invest. vol. 77, Jun. 1986, 1812-1816.

(Continued)

*Primary Examiner*—David Lukton
(74) *Attorney, Agent, or Firm*—Black Lowe & Graham PLLC

(57) ABSTRACT

PL37 (RAARISLGPRCIKAFTE [SEQ ID NO: 2]) is an Antisense Homology Box peptide composed of amino acids 37 to 53 of C5a-anaphylatoxin. Complementary peptides, ASGA-PAPGPAGPLRPMF (Pep-A [SEQ ID NO: 1]) and ASTA-PARAGLPRLPKFF (Pep-B [SEQ ID NO: 3]) were designed and characterized. Pep-A bound to PL37 and to C5a with very slow dissociation, whereas Pep-B failed to bind at all. C5a was inactivated by 7 nM or more of Pep-A and this concentration of Pep-A inhibited induction of intracellular $Ca^{++}$ influx in neutrophils. Patch clamp studies also showed the effectiveness of Pep-A in C5a-receptor-expressing neuroblastoma cells. Pep-A administration prevented rats from C5a-mediated rapid lethal shock. A-Pep-A (Pep-A acetylated with alanine at the amino-terminus) was more stable in vivo and showed stronger inhibition of inflammatory reactions in mice and rats. Chemical modification of Pep-A (e.g., acetylation, or single or multiple amino acid replacement, insertion, or deletion within the native Pep-A sequence) will yield effective inhibitors, and will often improve inhibitory function on C5a anaphylatoxin. In such modified constructs it will often be desired to conserve some or all 5 prolines found in Pep-A to preserve inhibitory function on C5a.

15 Claims, 5 Drawing Sheets

OTHER PUBLICATIONS

Sumichika, et al (2002), "Identification Of A Potent And Orally Active Non-Peptide C5a Receptor Antagonist." J. Biol. Chem. vol. 277, No. 51, 49403-49407.

Takizawa, et al, (1994), "Complement Inhibitor Of Rat Cell Membrane Resembling Mouse Crry/p65[1]." J. Immunol. 1994, 152:3032.

Fujita, et al, (2004), "Inactivation Of C5a Anaphylatoxin By A Peptide That Is Complementary To A Region Of C5a[1]." J. Immunol. 2004, 172:6382-6387.

* cited by examiner

US 7,763,708 B2

METHODS AND COMPOSITIONS FOR MODULATING C5-A-MEDIATED INFLAMMATORY RESPONSES

REFERENCE TO RELATED APPLICATIONS

This application is related to Provisional Application 60/601,038, filed on Aug. 12, 2004. Under 35 U.S.C. §119(e)(1), this application claims the benefit of said Provisional Application.

BACKGROUND OF THE INVENTION

Complement anaphylatoxin C5a is a 74-amino acid peptide generated from the fifth component of complement (C5) during complement activation (Ember et al., *Immunopharmacology* 38:3, 1997; Gerard, *Annu Rev Immunol.* 12:775, 1994). C5a acts efficiently as an anaphylatoxin stimulating cells such as leukocytes and endothelial cells, and is also a potent chemotactic factor for neutrophils and other inflammatory cells bearing C5a receptor (C5aR)[1]. Therefore, C5a is considered to be one of the most potent inflammatory mediators (Sumichika et al., *J. Biol. Chem* 277:49403, 2002). Inflammatory cells respond to nanomolar concentrations of C5a with intracellular calcium mobilization, stimulation of chemotaxis, aggregation, degranulation, and production of superoxide arions (Michael, *Immunological Reviews* 180: 177, 2001). Some inhibitors such as peptide or non-peptide C5a receptor antagonists and anti-C5a antibody have already been reported. However, the design of low molecular weight agents which directly inactivate C5a has been a challenging problem (Michael, *Immunological Reviews* 180:177, 2001).

[1] Abbreviations used herein: AHB, Antisense Homology Box; C-peptide, complementary peptide; EA, ethanolamine; EDC/NHS, N-ethyl-N-(dimethylaminopropyl) carbodiimide/N-hydroxysuccinimide; NHS, N-hydroxysuccinimide; Pep-A, Peptide-A; Pep-B; Peptide-B; PL37-MAP, PL37 in multiple antigenic peptide form; RU, resonance response; SPR, surface plasmon resonance.

PL37 is a complement C5a anaphylatoxin fragment (aa 37-53) and is an Antisense Homology Box (AHB) peptide of C5a (Baranyi et al., *Nature Med.* 1:894, 1995; Baranyi et al., *J. Immunol.* 157:4591, 1996). The sequences within the AHBs were based on the molecular recognition theory which states that peptides which are encoded on opposite strands of DNA in a given reading frame show affinity in binding each other and this binding occurs as a result of the hydropathic complementary of the peptides. In addition, such sense-antisense amino acid sequences might represent both intra- and intermolecular interaction sites. Approximately 8-15-amino acid-long regions of this type were found in proteins, which we termed Antisense Homology Boxes (AHB) (Baranyi et al., *Nature Med.* 1:894, 1995). PL37 is an AHB of C5a, however, it is also antisense to two regions of the C5aR (Baranyi et al., *J. Immunol.* 157:4591, 1996). PL37 in multiple antigenic peptide form (PL37-MAP) evoked inward calcium current pulses on human neuroblastoma TGW cells or dibutyryl cyclic AMP-treated U937 cells (Baranyi et al., *J. Immunol.* 157:4591, 1996; Farkas et al., *Neuroscience* 86:903, 1998).

Because of the important role that C5a plays in mediating inflammatory responses in mammalian subjects, there remains an important need in the art for methods and compositions that can be used to effectively modulate, i.e., inhibit, modify, or enhance, C5a-mediated inflammatory responses in these subjects for investigative, diagnostic, and/or therapeutic purposes.

SUMMARY OF THE INVENTION

The present invention satisfies this need and fulfills additional objects and advantages by providing novel peptides, peptide analogs and mimetics capable of binding C5a anaphylatoxin and modulating C5a activity. In certain exemplary embodiments, a C5a-modulatory peptide is provided that comprises an amino acid sequence ASGAPAPGPAGPLRPMF (SEQ ID NO: 1). Alternatively, a C5a-modulatory peptide may be selected for use within the methods and compositions of the invention that is modified from a reference peptide sequence (e.g., a reference sequence, such as ASGAPAPGPAGPLRPMF (SEQ ID NO: 1), designed as a complement to a native C5a peptide sequence), for example by deletion, insertion, or substitution of one or two amino acid residues within said reference or native complement sequence. Within additional aspects of the invention, the C5a-modulatory peptide can be modified by admixture with or conjugation to one or more additional amino acid(s), peptide (s), protein(s), and/or chemical reagent(s), which typically will not substantially impair C5a anaphylatoxin binding and modulating activities of the modified peptide. Within one exemplary modification, an amino terminal amino acid, e.g., an amino-terminal alanine, of said peptide is acetylated to improve in vivo half-life and/or activity of the peptide.

The novel C5a-modulatory peptides, peptide analogs and mimetics of the invention are typically selected for their ability to inhibit an inflammatory signal or activity of C5a exerted on an inflammatory cell or tissue bearing a C5a receptor (C5aR). In certain embodiments of the invention, a C5a-modulatory peptide is selected which inhibits an activity of C5a selected from stimulation of chemotaxis, aggregation, degranulation, and/or production of superoxide anions in a C5aR-bearing inflammatory cell or tissue (e.g., a C5aR-bearing leukocyte or endothelial cell or tissue).

Within additional embodiments of the invention, anti-inflammatory compositions are provided which may be used in investigative or diagnostic methods, or for administration to a mammalian cell or mammalian subject. The anti-inflammatory compositions typically comprise a peptide, peptide analog or mimetic capable of binding C5a anaphylatoxin and modulating an inflammatory activity of C5a. In certain embodiments, the compositions comprise a C5a modulatory peptide comprising an amino acid sequence ASGAPAPGPAGPLRPMF (SEQ ID NO: 1), or an amino acid sequence that is modified by deletion, insertion, or substitution of one or two amino acid residues within the sequence ASGAPAPGPAGPLRPMF (SEQ ID NO: 1). The compositions are effective to modulate a C5a-mediated inflammatory response in the mammalian cell or subject, and may be administered to the target cell or subject alone or in combination with a pharmaceutically acceptable carrier, delivery vehicle, excipient, or additional active (e.g., known anti-inflammatory) agent(s).

Within yet additional embodiments of the invention, methods for modulating an inflammatory response in a mammalian cell or mammalian subject are provided. The subject methods comprise administering an anti-inflammatory effective amount of a peptide, peptide analog or mimetic capable of binding C5a anaphylatoxin and modulating C5a activity. In certain embodiments, a C5a-modulatory peptide is employed in the subject methods, which peptide comprises an amino acid sequence ASGAPAPGPAGPLRPMF (SEQ ID NO: 1), or an amino acid sequence that is modified by deletion, insertion, or substitution of one or two amino acid residues within the sequence ASGAPAPGPAGPLRPMF (SEQ ID NO: 1). These methods are effective to modulate a C5a-mediated inflammatory response in a mammalian cell or subject.

DETAILED DESCRIPTION OF THE INVENTION

Figure 1:
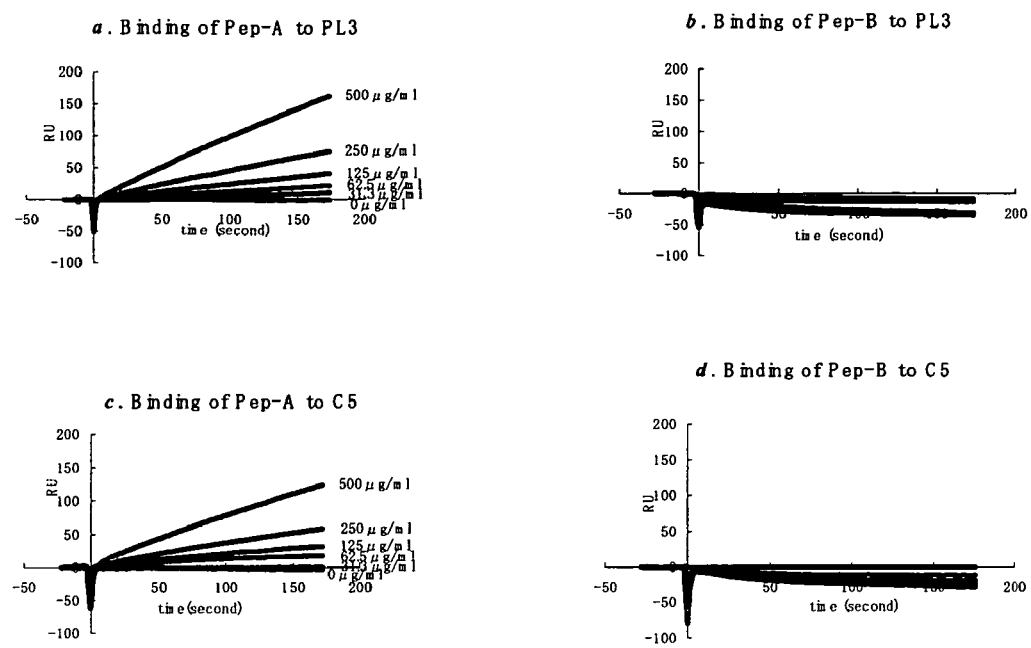
FIG. 1. Binding of C-peptides to immobilized PL37-MAP and C5a using Biacore equipment. An overlay plot of response curves obtained from the Biacore instrument when various concentrations of Pep-A and Pep-B were injected. All samples were injected at time 0, and the association was monitored as an increase in RU. a, Various concentrations of Pep-A were injected over the PL37-MAP-coupled flow cell. b, The same concentrations of Pep-B were also injected over the PL37-MAP-coupled flow cell. c, Pep-A was injected over the C5a-coupled flow cell at the same concentrations of Pep-A as in FIG. 1a. d, The same concentrations of Pep-B were also injected over the C5a-coupled flow cell.

Considering the important role of C5a in mediating inflammatory responses, initial investigations herein were directed toward production and analysis of C5a-binding molecules that could potentially block, impair, or enhance C5a-mediated inflammatory signaling or activation. As part of this investigative approach, complementary peptides (C-peptides) to PL37 were generated and selected for their potential to interfere with C5a function. To design the C-peptides, a software program MIMETIC (Campbell et al., *Microbiol. Immunol.* 46:211, 2002) was employed. The algorithm scores several physico-chemical parameters of each candidate peptide. C-peptides generated according to this general methodology have been reported to be inhibitory to HIV-1 reverse transcriptase (Campbell et al., *Microbiol. Immunol.* 46:211, 2002) and thrombomodulin (Shimomura et al., *Microbiol. Immunol.* 47:241, 2003).

Two C-peptides targeting PL-37 were designed, produced and characterized for use within the methods and compositions of the invention. These novel peptides were analyzed for their reactivity to PL37-MAP and C5a in various assays such as binding measurements, intracellular calcium mobilization, calcium influx and in an in vivo C5a-mediated lethal shock rat model (Takizawa et al., *J. Immunol.* 152:3032, 1994; Matsuo et al., *J. Exp. Med.* 180:1619, 1994; Mizuno et al., *J. Immunol.* 162:5477, 1999). The subject murine model is accepted in the art as a useful model predictive of C5a activity, and hence C5a-modulatory activity, in other mammalian subjects, including humans.

Design of C-Peptides

We used the evolutionary software program MIMETIC to design C-peptide sequences for interaction with PL37 (Farkas et al., *Neuroscience* 86:903, 1998). MIMETIC assigns a score using a genetic algorithm based on several physico-chemical parameters including hydropathic complementarity optimization, average structural similarity optimization, minimization of bulky side chain interference and backbone alignment. MIMETIC employs a genetic algorithm that generates a series of peptides by random alteration and by shuffling segments to optimize fitting to the target. MIMETIC then ranks the C-peptides according to their score. We synthesized the two highest score peptides, and tested their activity. Furthermore, we also synthesized peptides with an acetylated amino acid at the amino-terminal of the peptides.

Measurement of Binding Interactions by Surface Plasmon Resonance

Binding interactions between PL37 or C5a with C-peptides were evaluated using surface plasmon resonance (SPR) technology with the Biacore system. PL37 and C5a were covalently immobilized on the CM5 sensor chip by amine coupling methods using N-ethyl-N-(dimethylaminopropyl) carbodiimide/N-hydroxysuccinimide (EDC/NHS) according to the manufacturer's instructions. We activated the surface of the CM5 sensor chip with EDC/NHS for 20 min before injection with PL37-MAP (200 μg/ml in 10 mM sodium carbonate buffer, pH 8.5, over flow cell 2) or C5a (100 μg/ml in 10 mM acetate buffer, pH 5, over flow cell 3). Afterwards, excess NHS was deactivated for 20 min with 1 M ethanolamine hydrochloride (EA), pH 8.5. The reference flow cell was activated with EDC/NHS, and blocked with EA. Coupling was performed at a flow rate of 5 μl/min at 25° C. in PBS. Analyte (30 μl of C-peptide A or B) was injected at 10 μl/min at 25° C. in PBS. Binding interactions were determined by passing samples simultaneously over both the EA-blocked cell and the flow cell with immobilized PL37 or C5a so as to obtain units of resonance response (RU) by subtraction of the background using Biacore software (BIA evaluation).

Patch Clamp Measurements

The measurements were carried out on TGW human neuroblastoma cells bearing C5aR. Cells were voltage-clamped at room temperature at a holding potential of −70 mV using a whole cell clamp configuration. The instruments used for electrophysiology were as follows: an Axopatch 200-A patch clamp amplifier, a Digidata-1200 data acquisition system and pCLAMP 6.02 software from Axon Instruments Inc., (Foster City, Calif.). The head stage of the amplifier was fitted to an MHW-3 hydraulic manipulator manufactured by Narishige Inc. (Tokyo, Japan); and the cells were visualized using an Olympus IMT-2 invert microscope. Data acquisition and analysis were performed using an IBM compatible personal computer. Patch electrodes (OD=1.5 mm, thin wall, Garner Glass Co., Claremont, Calif.) were pulled with a PP-83 puller and polished with an MF-83 microforge (Narishige Inc). The resistance of patch electrodes was 8-10 MΩ. The solutions used were as follows: an extracellular solution (10 mM Hepes, 140 mM NaCl, 5 mM KCl, 2 mM $CaCl_2$, 2 mM $MgCl_2$, 10 mM glucose, pH=7.34) and an intracellular pipette solution (10 mM Hepes, 110 mM KCl, 15 mM NaCl, 0.1 mM $CaCl_2$, 2 mM $MgCl_2$, 1 mM EGTA, pH 7.25). Recordings were carried out on several cells (n=10 in each experiment) and were initiated simultaneously with the peptide application.

The PL37-MAP peptide or mixture of peptides (PL37-MAP and C-peptides) were incubated in an Eppendorf tube at room temperature for one hour in the extracellular solution and then applied to the cells via a puff pipette from a distance of 300-500 μm for 2 min.

Neutrophil Isolation

Neutrophils were isolated from fresh human blood with 0.2% EDTA as an anticoagulant. Whole blood was collected from a healthy volunteer (a collaborator of this study) via vein puncture. A 2.4 ml aliquot of blood was then layered onto 2 ml Mono-Poly Resolving Medium (Dainihon Seiyaku, Tokyo, Japan) in a centrifuge tube and centrifuged at 400 g for 20 min at room temperature. The polymorphonuclear leukocytes (neutrophils) were then harvested and the cell fraction was washed with Hanks' balanced salt solution (HBSS).

Intracellular $Ca^{++}$ Mobilization Measurement

The isolated neutrophils were loaded with 2 μM Fura-2/AM (Molecular Probes, Eugene, Oreg.) mixed with 0.02% Pluronic F-127 (Molecular Probes) and 0.2% DMSO in HBSS for 40 min at 37° C. The suspension was agitated to prevent sedimentation. After loading, the cells were washed with HBSS twice and suspended in HBSS containing 0.3% BSA (HBSS/BSA). Approximately $1 \times 10^6$ cells in 900 μl HBSS/BSA were added to a poly-L-lysine-coated 35 mm Petri dish and allowed to attach to the bottom of the dish for 30 min. Changes in intracellular calcium concentrations in response to C5a or a mixture of peptides (C-peptides and C5a) were determined by monitoring the ratio of fluorescence light emission at 510 nm as a result of excitation at 340 and 380 nm at 37° C. using an ARGUS HiSCA calcium imaging system (Hamamatsu Photonics, Hamamatsu, Japan). The mixture of peptides and C5a was incubated in an Eppendorf tube on ice for 30 min in the HBSS solution and then applied to the cells after a 2 min baseline recording.

Rat Lethal Shock Induced by Anti-Crry Antibody Following LPS Priming

Administration of anti-rat Crry mAb (5I2) (Takizawa et al., *J. Immunol.* 152:3032, 1994) induces lethal shock in rats primed with a trace amount of lipopolysaccharide (LPS) (Matsuo et al., *J. Exp. Med.* 180:1619, 1994; Mizuno et al., *J. Immunol.* 162:5477, 1999). With this model, all rats sensitized with 0.05 mg/kg of LPS died within 30 min of injection of mAb 5I2. Male Wistar rats weighing about 250 g were purchased from Chubu Kagaku Shizai (Nagoya, Japan) and were allowed free access to food and water. Each rat was injected with 0.05 mg/kg of LPS, prepared from a phenol extraction of *Salmonella typhosa* (Sigma Chemical Co., St. Louis, Mo.) in 250 μl saline. Then, 0.75 mg/kg of 5I2 was administered 20 h later. Ten minutes before the injection of 5I2, saline or C-peptides in saline were injected. All injections were intravenously administered through the tail vein. Animal experiments were carried out according to Nagoya City University Guideline for the Care and Use of Experimental Animals and approved by the Nagoya City University Graduate School of Medical Sciences Animal Care Committee.

C-Peptides Generated to a Target Peptide, PL37

Figure 2:
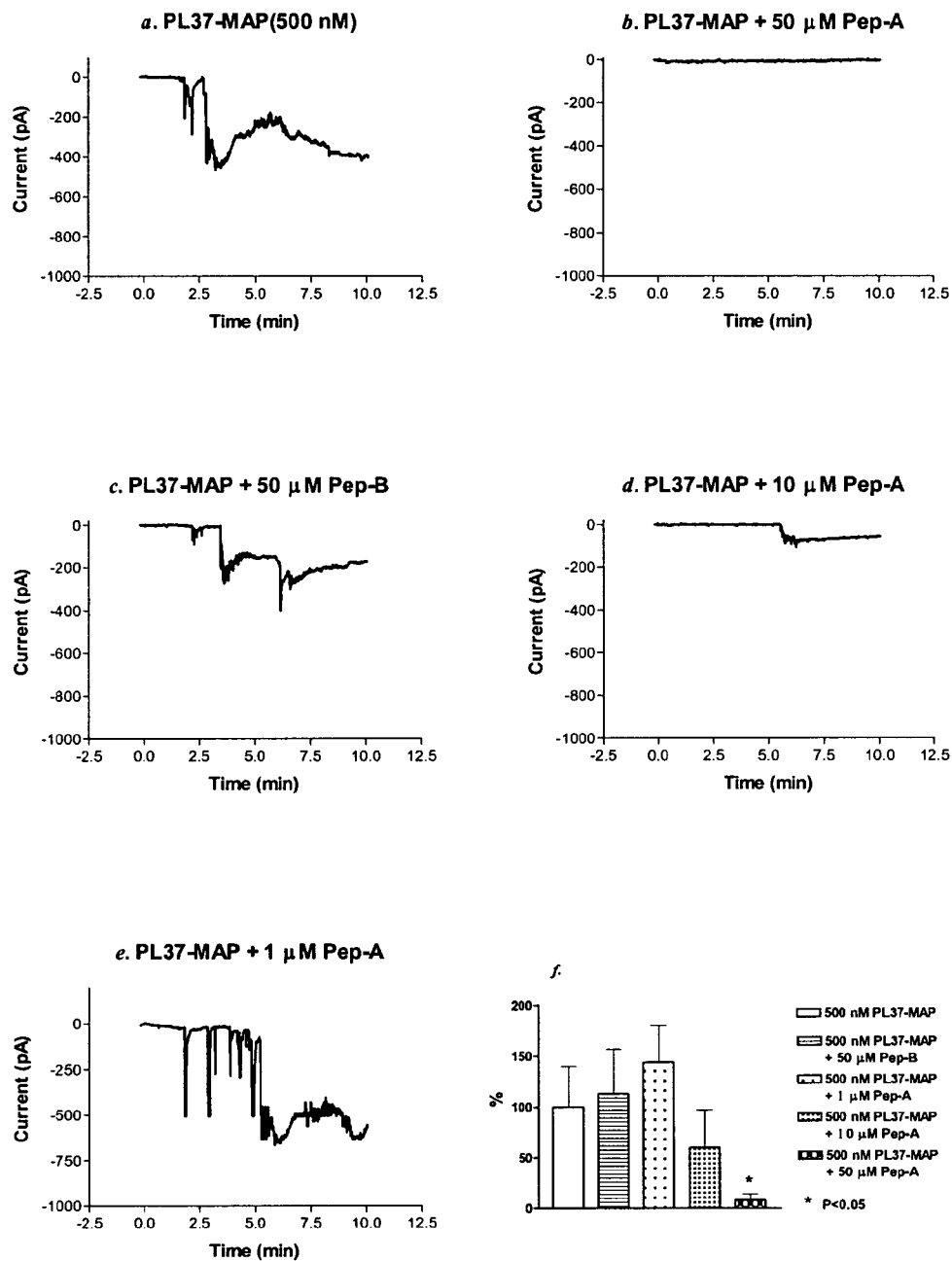
FIG. 2. Inward ion current pulses of human TGW cells treated with PL37-MAP and C-peptides. a, 500 nM PL37-MAP induced inward current pulses with an amplitude of 500 pA. b, When the PL37-MAP was mixed and incubated with 50 μM Pep-A, a pulse could not be induced. c, 50 μM Pep-B did not have any effect on the ion current evoked by PL37-MAP. d, A lower concentration (10 μM) of Pep-A partially inhibited the ion current triggered by PL37-MAP. e, When 1 μM of Pep-A was mixed and incubated with PL37-MAP, no inhibition was found. f, Concentration dependency of the area-under-curve data. This figure demonstrates that Pep-A had a significant and concentration-dependent effect on the ion current pulses induced by PL37-MAP.

The best-fit peptide sequences to the target region of C5a (sequence of PL37:RAARISLGPRCIKAFTE [SEQ ID NO: 2]) designed by MIMETIC were Peptide-A (Pep-A:ASGAPAPGPAGPLRPMF [SEQ ID NO: 1]) and Peptide-B (Pep-B:ASTAPARAGLPRLPKFF [SEQ ID NO: 3]). The acetylated Pep-A designated as A-Pep-A was prepared by acetylation of the N-terminal alanine of Pep-A.

Binding of C-Peptides to PL37-MAP and C5a

The Biacore instrument which uses SPR technology measures association and dissociation in real time of an unlabeled analyte with an immobilized ligand. PL37-MAP was covalently coupled to a CM5 sensor chip resulting in a net increase of 8,979 RU.

As analytes, Pep-A and Pep-B were injected over the PL37-MAP-coupled flow cell and to the flow cell coupled with EA only. All cycles were performed in PBS at 25° C. at a flow rate of 10 μl/min. As shown in FIG. 1*a*, binding data for the PL37-MAP-coupled flow cell were adjusted by subtraction of the data obtained by injection of the same sample over the EA-blocked flow cell (background). Pep-A bound to PL37-MAP, while Pep-B did not (FIG. 1*a*, 1*b*). Binding of Pep-A was concentration-dependent. Pep-A bound to PL37-MAP did not dissociate by increasing the salt concentration or by the addition of DMSO. 6 M urea treatment was required to dissociate the complex.

Binding of C-peptides to C5a was also examined. C5a was covalently coupled to a CM5 sensor chip resulting in a net increase of 5,770 RU. As analytes, Pep-A and Pep-B were injected over both the C5a-coupled and EA-coupled (as the control) flow cells. All cycles were performed in PBS at 25° C. at a flow rate of 10 μl/min. In FIG. 1*c*, the binding data for the C5a-coupled flow cell were adjusted by subtraction of the data obtained by injection of the same sample over the EA-blocked flow cell (background). Pep-A bound to C5a, whereas Pep-B did not (FIG. 1*d*). Binding of Pep-A was concentration-dependent. Furthermore, no dissociation of Pep-A bound to C5a was observed without treatment with 6 M urea.

$Ca^{++}$ Influx Measurement of TGW Cells

Inward calcium current pulses detected by a patch clamp assay were evoked when TGW cells were exposed to 500 nM PL37-MAP (FIG. 2*a*). However, 50 μM Pep-A inhibited the pulse almost completely (FIG. 2*b*). After washing out, 500 nM PL37-MAP alone were added to the same cells without incubation with C-peptide, and the PL37-MAP peptide triggered an ion current pulse (data not shown). Pep-B did not block the ion current evoked by PL37-MAP (FIG. 2*c*). Inhibition by Pep-A was concentration-dependent, since lower concentrations of the C-peptide blocked the effect of PL37-MAP only partially (FIG. 2*d-e*). When the cells were exposed to Pep-A alone, ion current could not be observed even at the highest concentration used (not shown). Normalized data for amplitudes of the ion current responses are shown in FIG. 2f.

Intracellular $Ca^{++}$ Mobilization Measurement of Neutrophils

Figure 3:
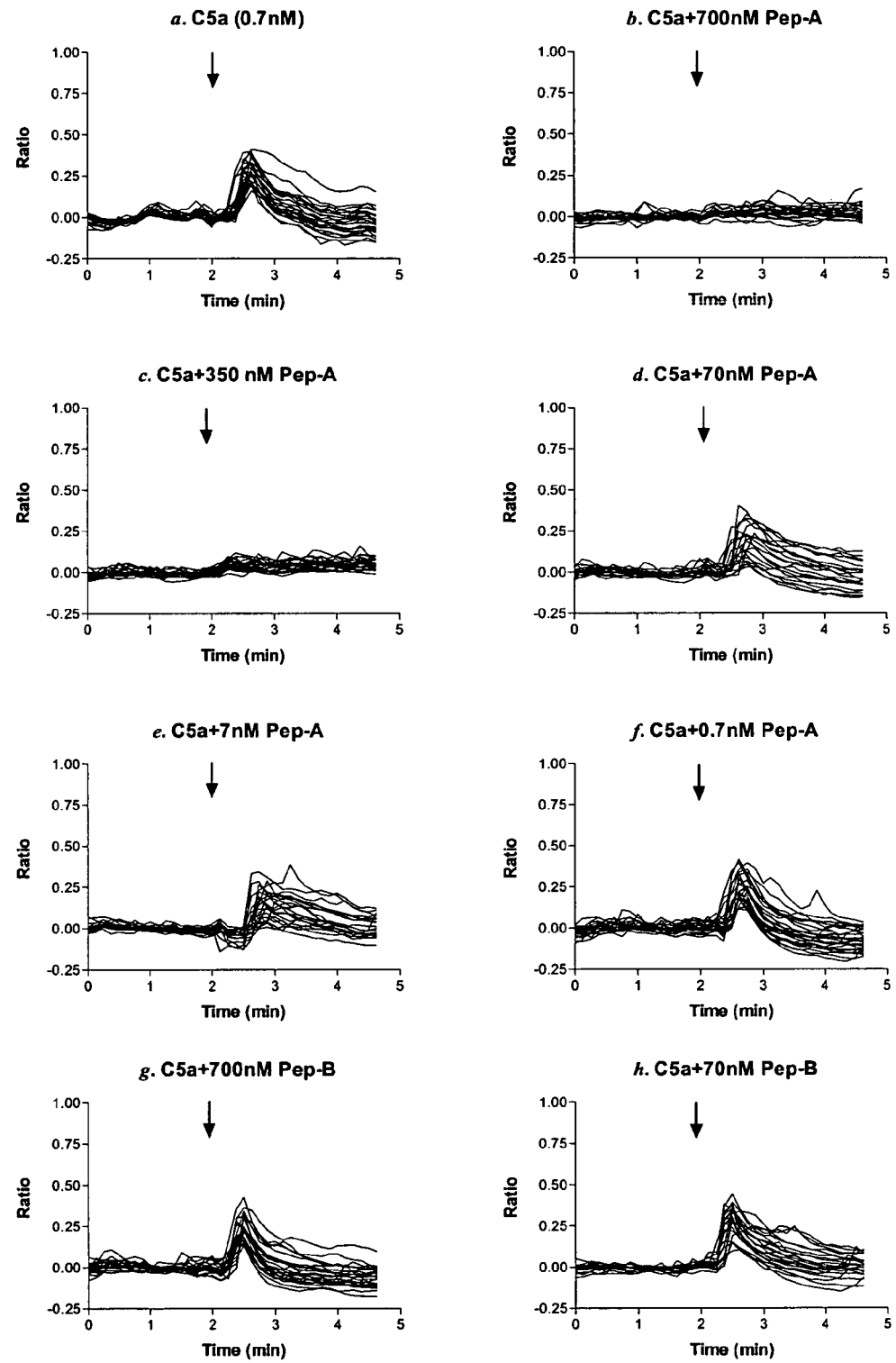
FIG. 3. Measurement of intracellular $Ca^{++}$ mobilization in neutrophils using a calcium imaging system. a. 0.7 nM C5a triggered a transient calcium influx in neutrophils. b. Incubation with 700 nM Pep-A blocked the effect of C5a completely. c. 95% inhibition was found when 350 nM Pep-A was incubated with C5a. d, e. Lower concentrations of Pep-A (70 or 7 nM) caused partial inhibition. f. The inhibitory effect was not detected when 0.7 nM Pep-A was mixed with C5a. g, h. Pep-B (700 or 70 nM) failed to cause inhibition of the calcium influx triggered by C5a. The area-under-curve data show the concentration dependency of the inhibitory effect of Pep-A.
Figure 4:
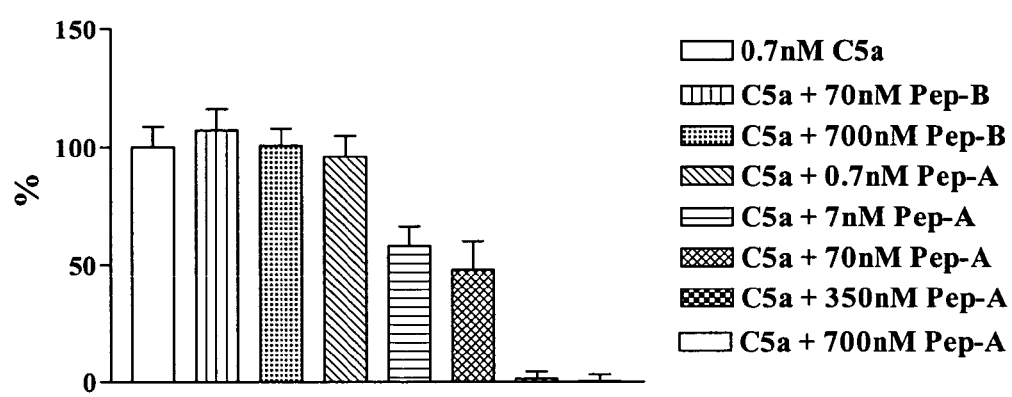
FIG. 4. The area-under-curve graph of the data of FIG. 3 show the concentration dependency of the inhibitory effect of Pep-A.
Figure 5:
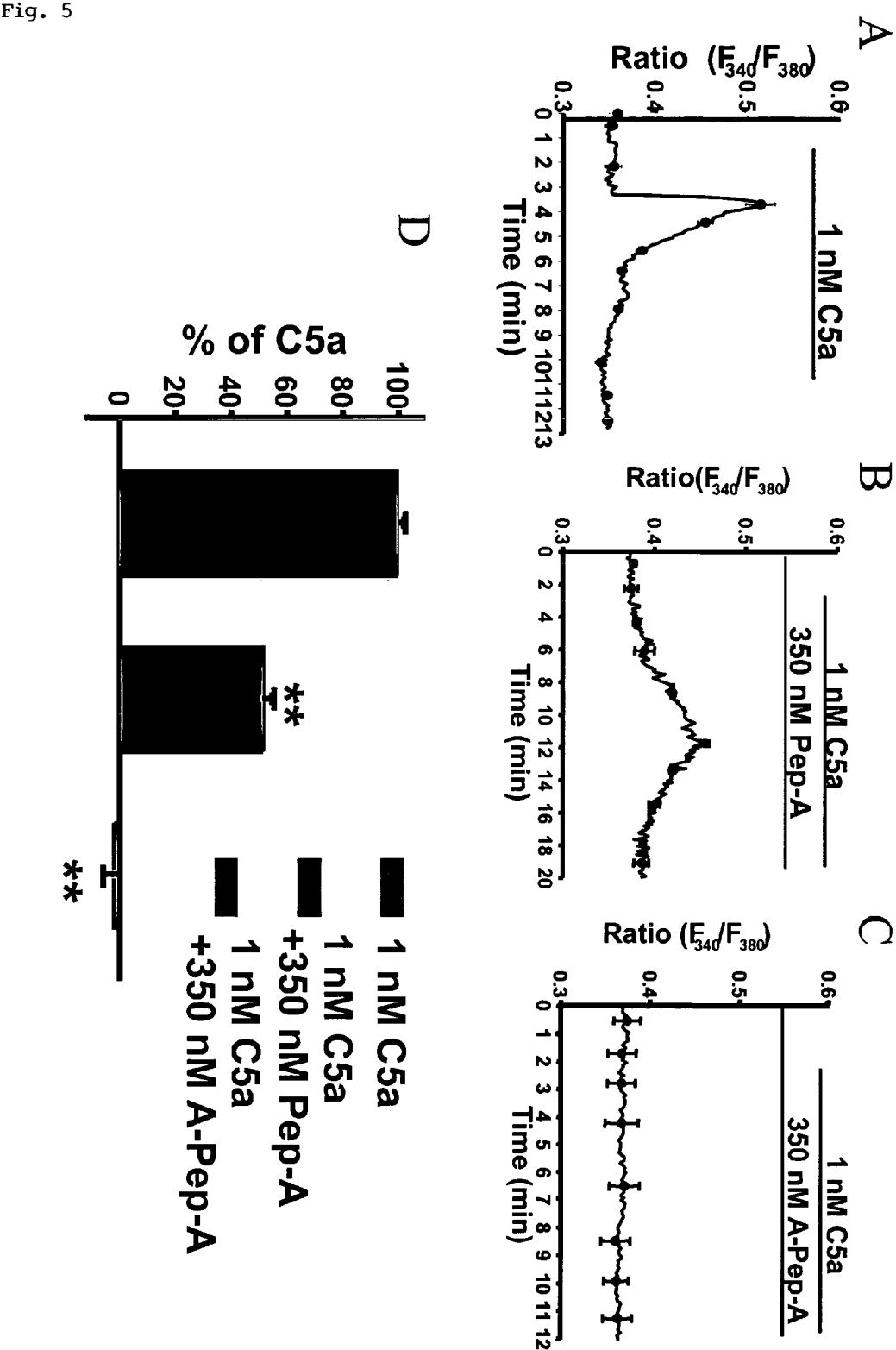
FIG. 5. Intracellular $Ca^{++}$ Mobilization Measurement of Neutrophils. The effect of Pep-A and A-Pep-A on C5a function was analyzed by $Ca^{++}$ mobilization measurements using an ARGUS HiSCA Calcium Imaging System. Administration of 1 nM recombinant human C5a induced a transient increase in the level of intracellular $Ca^{++}$ in human neutrophils (FIG. 5A). The level of this activation was about 50% of the maximum achieved with a higher concentration of C5a. Incubation with 350 nM of Pep-A and C5a significantly inhibited $Ca^{++}$ (FIG. 5B). Incubation with 350 nM A-Pep-A completely inhibited C5a in the $Ca^{++}$ mobilization test (FIG. 5C). The normalized results using the area-under-curve data of the calcium influx are summarized in FIG. 5D.

The effect of C-peptides on C5a function was analyzed by measuring $Ca^{++}$ mobilization using an ARUGUS HiSCA calcium imaging system. Administration of 0.7 nM recombinant human C5a (RhC5a) induced a transient increase in the level of intracellular $Ca^{++}$ of human neutrophils (FIG. 3a). The level of this activation was about 50% of the maximum achieved with higher concentrations of C5a. A mixture of C-peptide and C5a was incubated in an Eppendorf tube on ice for 30 min in the HBSS solution and then applied to the cells. Incubation of C5a with 700 nM of Pep-A inhibited the $Ca^{++}$ mobilization almost completely (FIG. 3b). A lower concentration of Pep-A (350 nM) still inhibited about 95% of the effect of C5a (FIG. 3c). Inhibition was therefore concentration-dependent: lowering the concentration of Pep-A resulted in a higher amplitude of calcium influx triggered by C5a (FIG. 3d,e). The inhibitory effect of Pep-A disappeared at 0.7 nM (FIG. 3f). However, incubation of C5a with Pep-B showed no inhibition at any concentration used (700 and 70 nM of Pep-B; FIG. 3g,h). The results were normalized results using the area-under-curve data of the calcium influx and are described in FIG. 4. A-Pep-A (acetylated Pep-A) was compared with Pep-A in its inhibitory effect on C5a; A-Pep-A showed a much stronger effect than Pep-A (FIG. 5).

Effect of C-Peptides in a Rat Lethal Shock Model

Administration of 0.75 mg/kg anti-rat Crry monoclonal antibody (Takizawa et al., J. Immunol. 152:3032, 1994) induces rapid lethal shock in rats primed with 0.05 mg/kg of LPS 20 h earlier (Matsuo et al., J. Exp. Med. 180:1619, 1994; Mizuno et al., J. Immunol. 162:5477, 1999). The lethal outcome was found to be C5a-mediated (Mizuno et al., J. Immunol. 162:5477, 1999). In order to investigate the inhibitory effect of the C-peptides in this model, we injected rats with saline (for the control) or C-peptides in 250 µl of saline 10 min before the 5I2 injection. All rats injected with saline died within 30 min (Table 1). However, all rats injected with 4 mg/kg of Pep-A survived. The inhibition was concentration-dependent: lowering the concentration of Pep-A (from 2 mg/kg to 1 mg/kg) resulted in a lower proportion of the surviving rats. Some of the surviving rats stopped breathing briefly in the first 1 or 2 min after injection of 5I2, but were soon breathing again and about 20-40 min later began moving. When the LPS sensitized rats were treated with Pep-A without anti-Crry mAb administration, the animals survived with no harmful effect of Pep-A. On the other hand, all rats injected with antibody and 4 mg/kg of Pep-B died, as did those treated with the saline control.

TABLE 1

Effect of C-Peptides On The Rat Lethal Shock Model

| C-peptides* | Surviving/total number of rats | Survival rate (%) |
|---|---|---|
| Saline alone | 0/8** | 0 |
| Pep-B 4 mg/kg | 0/4 | 0 |
| Pep-A 4 mg/kg | 4/4** | 100 |
| 2 mg/kg | 2/3 | 67 |
| 1 mg/kg | 1/3 | 33 |
| 0.5 mg/kg | 3/4 | 75 |

*C-peptides in 250 µl saline were intravenously injected 10 min before the intravenous injection of anti-Crry monoclonal antibody.
**Saline control and Pep-A 4/mg/kg are statistically significant (p < 0.003: Fisher's method).

Peptide Analogs and Mimetics

The C5a-modulatory peptides of the present invention include peptides designed as a direct complementary sequence to a native C5a sequence (i.e., peptides designed for optimal hydropathic complementary to an exact, native peptide sequence of C5a, or an allelic variant thereof). In alternate embodiments, the C5a-modulatory peptides can be selected from chemically or recombinantly modified "analogs" or "mimetics" of such direct complementary sequences, for example peptide fragments of direct complementary sequences, or peptide analogs comprising such a direct complementary sequence as modified by single or multiple amino acid deletions, insertions, rearrangements, or substitutions. C5a-modulatory peptide analogs thus modified exhibit substantial C5a binding and/or modulatory activity comparable to that of a corresponding direct complementary peptide, which is activity that is at least 50%, typically at least 75% or greater, compared to activity of the corresponding direct complementary peptide.

For purposes of the present invention, the term C5a-modulatory peptide "analog" thus includes derivatives or synthetic variants of a C5a binding peptide (direct complement or "reference" peptide), such as amino and/or carboxyl terminal deletions, extensions, and fusions, as well as intrasequence insertions, substitutions or deletions of single or multiple amino acids. Insertional amino acid sequence variants are those in which one or more amino acid residues are introduced into a predetermined site in the direct complement or reference peptide. Random insertion is also possible with suitable screening of the resulting product. Deletional variants are characterized by removal of one or more amino acids from the sequence. Substitutional amino acid variants are those in which at least one residue in the sequence has been removed and a different residue inserted in its place.

Where a direct complement or reference C5a-modulatory peptide is modified by amino acid substitution, amino acids are generally replaced by other amino acids having similar, conservatively-related chemical properties such as hydrophobicity, hydrophilicity, electronegativity, bulky side chains and the like. Residue positions which are not identical to the native peptide sequence are thus replaced by conservative amino acids having similar chemical properties, such as charge or polarity, which changes are not likely to substantially affect the properties of the peptide analog. These and other minor alterations substantially maintain the C5a binding and/or C5a modulatory activity of the direct complement or reference peptide. Alternatively, useful peptide analogs can be selected and tested for activity within the methods and compositions of the invention based on conservation of immunological cross-reactivity with an antibody that recognizes the direct complement or reference peptide.

The term "conservative amino acid substitution" refers to the general interchangeability of amino acid residues having similar side chains. For example, a group of conservatively-related amino acids having aliphatic side chains is alanine, valine, leucine, and isoleucine; a group of conservatively-related amino acids having aliphatic-hydroxyl side chains is serine and threonine; a group of a group of conservatively-related amino acids having amide-containing side chains is asparagine and glutamine; a group of conservatively-related amino acids having aromatic side chains is phenylalanine, tyrosine, and tryptophan; a group of conservatively-related amino acids having basic side chains is lysine, arginine, and histidine; and a group of conservatively-related amino acids having sulfur-containing side chains is cysteine and methionine.

C5a-modulatory peptide analogs also include modified forms of a direct complement or reference, C5a-modulatory peptide incorporating stereoisomers (e.g., D-amino acids) of the twenty conventional amino acids, or unnatural amino acids such as α,α-disubstituted amino acids, N-alkyl amino acids, lactic acid. These and other unconventional amino acids may also be substituted or inserted within peptides of the present invention. Examples of unconventional amino acids include: 4-hydroxyproline, γ-carboxyglutamate, ε-N,N, N-trimethyllysine, ε-N-acetyllysine, O-phosphoserine, N-acetylserine, N-formylmethionine, 3-methylhistidine, 5-hydroxylysine, ω-N-methylarginine, and other similar amino acids and amino acids (e.g., 4-hydroxyproline). For purposes of the present invention, analogs of C5a-modulatory peptides also include single or multiple substitutions, deletions and/or additions of carbohydrate, lipid and/or proteinaceous moieties that occur naturally or artificially as structural components of direct complement or reference peptides or are bound or otherwise associated with the peptide analog.

C5a-modulatory peptides and peptide analogs within the invention are typically between about 6-50 amino acid residues in length, more typically between about 10-35 amino acid residues in length, and most often between about 15-25 amino acid residues in length. In more specific embodiments, peptides are 12, 13, 15, 17, 21, 22, amino acid residues in length.

Within additional aspects of the invention, C5a-modulatory peptide mimetics are provided which comprise a peptide or non-peptide molecule that mimics the tertiary binding structure and activity of a direct complement or reference C5a binding peptide (e.g., of exemplary reference peptide ASGA-PAPGPAGPLRPMF [SEQ ID NO: 1]) described herein. These peptide mimetics include recombinantly or chemically modified peptides, as well as non-peptide agents such as small molecule drug mimetics.

In one aspect, peptides of the invention are modified to produce peptide mimetics by replacement of one or more naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from 5 members to 4, 6, or 7 members. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl.

The peptides of the invention, including peptidomimetics, can also be covalently bound to one or more of a variety of nonproteinaceous polymers, e.g., polyethylene glycol, polypropylene glycol, or polyoxyalkenes, in the manner set forth in U.S. Pat. No. 4,640,835; U.S. Pat. No. 4,496,689; U.S. Pat. No. 4,301,144; U.S. Pat. No. 4,670,417; U.S. Pat. No. 4,791,192; or U.S. Pat. No. 4,179,337, all which-are incorporated by reference in their entirety herein.

Other peptide analogs and mimetics within the invention include glycosylation variants, and covalent or aggregate conjugates with other chemical moieties. Covalent derivatives can be prepared by linkage of functionalities to groups which are found in amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins, e.g., immunogenic moieties may also be employed.

In certain embodiments, glycosylation alterations of C5a-modulatory peptides are included, which can be made, e.g., by modifying the glycosylation patterns of a peptide during its synthesis and processing, or in further processing steps. Particularly preferred means for accomplishing this are by exposing the peptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents.

Peptidomimetics may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

A major group of peptidomimetics within the invention are covalent conjugates of C5a-modulatory peptides, or fragments thereof, with other proteins or peptides. These derivatives can be synthesized in recombinant culture such as N- or C-terminal fusions or by the use of agents known in the art for their usefulness in cross-linking proteins through reactive side groups. Preferred peptide and protein derivatization sites for targeting by cross-linking agents are at free amino groups and carbohydrate moieties.

Fusion polypeptides between C5a-modulatory peptides and other homologous or heterologous peptides and proteins are also provided. Many growth factors and cytokines are homodimeric entities, and a repeat construct of a C5a-modulatory peptide linked to form "cluster peptides" will yield various advantages, including lessened susceptibility to proteolytic degradation. Various alternative multimeric constructs comprising peptides of the invention are also provided. In one embodiment, various polypeptide fusions are provided as described in U.S. Pat. Nos. 6,018,026 and 5,843,725, by linking one or more C5a-modulatory peptides of the invention with a heterologous, multimerizing polypeptide or protein, for example, immunoglobulin heavy chain constant region, or an immunoglobulin light chain constant region. The biologically active, multimerized polypeptide fusion thus constructed can be a hetero- or homo-multimer, e.g., a heterodimer or homodimer, which may each comprise one or more distinct C5a-modulatory binding peptide(s) of the invention. Other heterologous polypeptides may be combined with the C5a-modulatory peptide(s) to yield fusions comprising, e.g., a hybrid protein exhibiting heterologous (e.g., CD4 or CD8 receptor) binding specificity. Likewise, heterologous fusions may be constructed that exhibit a combination of properties or activities of the derivative proteins. Other typical examples are fusions of a reporter polypeptide, e.g., CAT or luciferase, with a C5a-modulatory peptide of the invention, to facilitate localization of the fused protein (see, e.g., Dull et al., U.S. Pat. No. 4,859,609, incorporated herein by reference). Other gene/protein fusion partners useful in this context include bacterial beta-galactosidase, trpE, Protein A, beta-lactamase, alpha amylase, alcohol dehydrogenase, and yeast alpha mating factor (see, e.g., Godowski et al., *Science* 241:812-16, 1988, incorporated herein by reference).

The present invention also contemplates the use of C5a-modulatory peptides modified by covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful for various purposes, for example as immunogens, as reagents in immunoassays, or in purification methods such as for affinity purification of ligands or other binding partners. Within exemplary embodiments, C5a-modulatory peptides are immobilized by covalent bonding to a solid support such as cyanogen bromide-activated Sepharose, or adsorbed onto polyolefin surfaces, with or without glutaraldehyde cross-linking, for use in assay, diagnostic, purification, or cytometric methods.

Those of skill in the art recognize that a variety of techniques are available for constructing peptide mimetics with the same or similar desired biological activity as the corresponding peptide compound but with more favorable activity than the peptide with respect to solubility, stability, and/or susceptibility to hydrolysis and proteolysis (see, e.g., Morgan and Gainor, *Ann. Rep. Med. Chem.* 24:243-52, 1989, incorporated herein by reference). Exemplary peptide mimetics in this context can be modified at the N-terminal amino group, the C-terminal carboxyl group, and/or by changing one or more amido linkages in the peptide to a non-amido linkage. Two or more such modifications can be coupled in one peptide mimetic structure (e.g., modification at the C-terminal carboxyl group and inclusion of a —CH2-carbamate linkage between two amino acids in the peptide.

For N-terminal modifications, the peptides typically are synthesized as a free acid, but can be readily prepared as the amide or ester. One can also modify the amino and/or carboxy terminus of the peptide compounds of the invention to produce other compounds of the invention. Exemplary amino terminus modifications include methylating (i.e., —NHCH3 or —NH(CH3)2), acetylating, adding a carbobenzoyl grout, or blocking the amino terminus with any blocking group containing a carboxylate functionality defined by RCOO—, where R is selected from the group consisting of naphthyl, acridinyl, steroidyl, and similar groups. Exemplary carboxy terminus modifications include replacing the free acid with a carboxamide group or forming a cyclic lactam at the carboxy terminus to introduce structural constraints.

One can also cyclize the C5a-modulatory peptides of the invention, or incorporate a desamino or descarboxy residue at one or more termini of the peptide, so that there is no terminal amino or carboxyl group, to decrease susceptibility to proteases or to restrict the conformation of the peptide. Useful C-terminal functional groups in this context include amide, amide lower alkyl, amide di(lower alkyl), lower alkoxy, hydroxy, and carboxy, and the lower ester derivatives thereof, and the pharmaceutically acceptable salts thereof.

Other methods for making peptide derivatives and mimetics of the invention are described in Hruby et al. *Biochem J.* 268(2):249-62, 1990, incorporated herein by reference). According to these methods, the anti-coreceptor binding peptide compounds of the invention also serve as structural models for non-peptide mimetic compounds with similar biological activity. Those of skill in the art recognize that a variety of techniques are available for constructing compounds with the same or similar desired biological activity as a lead peptide compound but with more favorable activity than the lead with respect to solubility, stability, and susceptibility to hydrolysis and proteolysis (see, e.g., Morgan and Gainor, *Ann. Rep. Med. Chem.* 24:243-52, 1989, incorporated herein by reference). These techniques include replacing the peptide backbone with a backbone composed of phosphonates, amidates, carbamates, sulfonamides, secondary amines, and/or N-methylamino acids.

Peptide mimetics wherein one or more of the peptidyl linkages [—C(O)NH—] have been replaced by such linkages as a —CH2-carbamate linkage, a phosphonate linkage, a —CH2-sulfonamide linkage, a urea linkage, a secondary amine (—CH2NH—) linkage, and an alkylated peptidyl linkage [—C(O)NR6- where R6 is lower alkyl] are prepared during conventional peptide synthesis by merely substituting a suitably protected amino acid analogue for the amino acid reagent at the appropriate point during synthesis. Suitable reagents include, for example, amino acid analogues wherein the carboxyl group of the amino acid has been replaced with a moiety suitable for forming one of the above linkages.

The C5a-modulatory peptides and peptide analogs and mimetics of the invention can be used for screening (e.g., in kits and/or screening assay methods) to identify additional compounds, including other peptides and peptide mimetics as well as small molecule drugs, that will function as C5a-modulatory agents within the methods and compositions of the invention. Several methods employing automated assays have been developed to permit screening of tens of thousands of such candidate compounds in a short period (see, e.g., Fodor et al., *Science* 251:767-73, 1991, and U.S. Pat. Nos. 5,677,195; 5,885,837; 5,902,723; 6,027,880; 6,040,193; and 6,124,102, issued to Fodor et al., each incorporated herein by reference). For example, large combinatorial libraries of the compounds can be constructed by the encoded synthetic libraries (ESL) method described in, e.g., WO 95/12608, WO 93/06121, WO 94/08051, WO 95/35503, and WO 95/30642 (each incorporated by reference). Peptide libraries can also be generated by phage display methods (see, e.g., Devlin, WO 91/18980, incorporated herein by reference). Many other publications describing chemical diversity libraries and screening methods are also considered reflective of the state of the art pertaining to these aspects of the invention and are generally incorporated herein.

In one general screening strategy within the invention, new C5a-modulatory agents (agonists and antagonists) can be readily identified using the C5a-modulatory peptides of the invention incorporated within highly automated assay methods. Of particular importance are antagonist compounds that inhibit, block, or enhance C5a-mediated inflammatory signaling or activity. One method of screening for new C5a-modulatory agents (e.g., small molecule drug peptide mimetics) utilizes eukaryotic or prokaryotic host cells which are stably transformed with recombinant DNA molecules expressing a C5a-modulatory peptide. Such cells, either in viable or fixed form, can be used for standard binding assays (see, e.g., Parce et al., *Science* 246:243-47, 1989; and Owicki et al., *Proc. Natl. Acad. Sci. USA* 87:4007-11, 1990, each incorporated herein by reference). Competitive assays are particularly useful, where the cells are contacted and incubated with a labeled reagent (e.g., a labeled receptor or antibody) having known binding affinity to the peptide ligand, and a test compound or sample whose binding affinity is being measured. The bound and free labeled binding components are then separated to assess the degree of ligand binding. Another technique for drug screening within the invention involves an approach which provides high throughput screening for compounds having suitable binding affinity to a target molecule, e.g., C5a or a C5a receptor, as described in detail in Geysen, European Patent Application 84/03564, published on Sep. 13, 1984; Fodor et al., Science 251:767-73, 1991, and U.S. Pat. Nos. 5,677,195; 5,885,837; 5,902,723; 6,027,880; 6,040,193; and 6,124,102, issued to Fodor et al.

Within one exemplary embodiment illustrating construction of useful C5a-modulatory peptide analogs and mimetics from a direct C5a complement peptide (or reference C5a-modulatory peptide sequence), an acetylated derivative of Pep-A (A-Pep-A) was constructed and tested for use within the methods and compositions of the invention. A-Pep-A is a peptide with the same sequence as that of Pep-A with acetylated alanine at the amino-terminal amino acid. Effect of A-Pep-A was tested on the lethal shock of mice induced by intravenous administration of CAWS (Candida albicans water soluble extract). The lethal shock is complement mediated since it does not occur in C5 deficient mice. ICR mice were injected with 4 mg/kg of A-Pep-A intraperitonally (i.p.) or intravenously (i.v.) 10 min before i.v. challenge with 200 µg of 100 µg CAWS. Although Pep-A did not show any effect on the lethal shock; i.v. administration of 4 mg/kg A-Pep-A rescued half of mice challenged with 100 µg CAWS as shown in Table 2. Effect of A-Pep-A was also evaluated on the skin reaction of rats. As an indicator dye of vascular exudation, rats were i.v. injected with 0.5 ml of Evans Blue (8 mg/ml in saline) 30 min before intradermal (i.d.) injection of 5 µg 512 (anti-Crry monoclonal antibody) together with Pep-A, A-Pep-A of saline control). As shown in Table 3, A-Pep-A suppressed the dye exudation although Pep-A was not effective in the inhibition of the skin inflammation.

TABLE 2

| Date | Pre | Dose | Route | CAWS | Dead/total |
|---|---|---|---|---|---|
| 2004.2.14 | Saline | 200 µL | i.p. | 200 µg/mouse | 3/3 |
|  | A-PepA | 4 mg/kg | i.p. | 200 µg/mouse | 3/3 |
|  | A-PepA | 4/mg/kg | i.v. | 200 µg/mouse | 3/3 |
| 2004.2.16 | Saline | 200 µL | i.p. | 100 µg/mouse | 3/3 |
|  | A-PepA | 4 mg/kg | i.p. | 100 µg/mouse | 3/3 |
|  | A-PepA | 4/mg/kg | i.v. | 100 µg/mouse | 2/4 |

TABLE 3

| 5I2 dose | Pep-A | A-Pep-A | Blue spots at 30 min* | Blue spots at 2 h** |
|---|---|---|---|---|
| 2.5 µg | 40 µg |  | ++ | 7 +/− 2 |
| 2.5 µg |  | 40 µg | − | 3 +/− 1 |
| 2.5 µg | 4 µg |  | ++ |  |
| 2.5 µg |  | 4 µg | − |  |
| 2.5 µg |  |  | ++ |  |
| 5.0 µg | 40 µg |  | +++ |  |
| 5.0 µg |  | 40 µg | − |  |
| 5.0 µg | 4 µg |  | +++ |  |
| 5.0 µg |  | 4 µg | + |  |
| 5.0 µg |  |  | +++ |  |

*By inspection from the outer surface 30 min after intradermal injection.
**Measured the spots from reverse side of the skin following removal 2 h after the intradermal injection.

Various C5aR antagonists have been reported previously; and some of these interfered with C5a-mediated functions in vitro and in vivo (Sumichika et al., J. Biol. Chem. 277:49403, 2002; Kontcatis et al., J. Immunol. 153:4200, 1994; Kondo et al., Clin Exp Immunol 124:323, 2001; Pellas et al., J. Immunol 160:5616, 1998). However, the only reported inhibitors of C5a were anti-C5a antibodies (Stevens et al., J. Clin Invest 77:1812, 1986; Hatherill et al., J. Biol. Response Mod 8:614, 1989; Czermak et al., Nat. Med. 5:788, 1999). In this study, we designed C-peptides expecting them to interact directly with C5a resulting in abrogation of C5a function. Two peptides, Pep-A and Pep-B; were designed by the computer program MIMETIC to target PL37, an AHB region of human C5a (pp. 37-53). Pep-A bound to the target PL37 as determined using surface plasmon resonance technology, and inhibited the inward ion current pulse induced by PL37-MAP in neuroblastoma cells and C5a induction of intracellular $Ca^{++}$ mobilization in neutrophils. Furthermore, Pep-A bound to the whole C5a molecule so strongly that the complex could only be dissociated with 6M urea.

Although Pep-B was designed using the same method as used for Pep-A, and although both Pep-A and Pep-B showed maximum best-fit values using MIMETIC, Pep-B showed no reactivity with PL37-MAP or C5a in any assay carried out. Careful examination of Pep-A and Pep-B might therefore provide useful information for improvement of the algorithm. Furthermore, the information obtained will contribute to a better understanding of peptide characteristics necessary to ensure interaction with a target amino acid sequence.

Two binding sites in C5a to C5aR have been reported. One is at the core of C5a and is centered around Arg40 (Mollison et al., Proc Natl Acad Sci USA 86:292, 1989). The other is contained in the eight amino acids of the C-terminal (Kawai et al., J. Med Chem. 34:2068, 1991). PL37 is located around the first binding site. Pep-A was designed against the PL37 sequence of C5a and inhibited the function of both C5a and PL37. Therefore, our data demonstrates that this AHB-derived PL37 is an important region in C5a.

Treatment with Pep-A was effective in our rat lethal shock model. In this model, rats primed with LPS died within 30 min when injected with anti-Crry mAb. In addition, the lethal outcome was mediated by C5a (Mizuno et al., J. Immunol. 162:5477, 1999). Hence our data suggest that Pep-A might bind selectively to C5a in vivo. However, one weak point of using peptide drugs is their short half-life in vivo. Therefore, a time delay between triggering shock and administration of the peptide could be crucial. Administration of 4 mg/kg of Pep-A 30 min before the injection of anti-Crry mAb was not effective indicating that Pep-A had been degraded in 30 min in vivo. The variable results at lower concentration of Pep-A (Table 1) could be due to the short half-life of the peptide in vivo. On the other hand, this short half-life could be advantageous. In endotoxic shock, endotoxin induces transient activation of complement and generation of C5a and C3a fragments which cause lethal shock. In this form of shock, the short duration of the peptide drug and its rapid clearance would be an advantage in avoiding possible long-lasting side effects. Indeed, rats injected with Pep-A survived without any noticeable deleterious side effects. In the lethal shock model of mouse induced by i.v. administration of CAWS, A-Pep-A rescued mice to some extent (Table 2) although Pep-A was not effective. In the experiment of skin inflammation induced by i.d. injection of anti-Crry antibody (5I2), A-Pep-A could inhibit the local inflammation although Pep-A was not effective (Table 3). These results indicate that some chemical modifications of Pep-A such as acetylation improve the in vivo effect of Pep-A. Therefore, chemical modification of Pep-A such as acetylation will improve the inhibitory function on C5a anaphylatoxin and one or two amino acid replacement of Pep-A will also be effective. Out of 17 amino acids, Pep-A has 5 prolines that restrict the structure of peptides. In certain embodiments, it will be desirable to conserve all or a majority of the 5 prolines in Pep-A to optimize inhibitory function of peptides and peptide analogs on C5a.

Although the foregoing invention has been described in detail by way of example, it will be apparent to the artisan that certain changes and modifications may be practiced within the scope of the appended claims, which are presented by way of illustration not limitation.

All publications mentioned herein are incorporated herein by reference in their entirety for the purpose of describing and disclosing, for example, the methods and methodologies that are described in the publications which can be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed:

1. A peptide capable of binding C5a anaphylatoxin and inhibiting C5a activity, comprising an amino acid sequence ASGAPAPGPAGPLRPMF (SEQ ID NO: 1).

2. The peptide of claim 1, wherein an N-terminal amino acid of said peptide is acetylated.

3. The peptide of claim 1, wherein said peptide inhibits an inflammatory signal or activity of C5a exerted on an inflammatory cell or tissue bearing a C5a receptor (C5aR).

4. The peptide of claim 3, wherein said activity of C5a inhibited by said peptide is selected from stimulation of chemotaxis, aggregation, degranulation, and/or production of superoxide anions in said C5aR-bearing inflammatory cell or tissue.

5. An anti-inflammatory composition for administration to a mammalian subject, comprising a pharmaceutically acceptable carrier and a peptide capable of binding C5a anaphylatoxin and inhibiting an inflammatory activity of C5a, wherein the peptide comprises an amino acid sequence ASGAPAPGPAGPLRPMF (SEQ ID NO: 1), and wherein said composition is effective to inhibit a C5a-mediated inflammatory response in said mammalian subject.

6. The anti-inflammatory composition of claim 5, wherein the peptide comprises the amino acid sequence ASGAPAPGPAGPLRPMF (SEQ ID NO: 1).

7. The anti-inflammatory composition of claim 5, wherein an amino terminal amino acid of said peptide is acetylated.

8. The anti-inflammatory composition of claim 5, wherein said peptide inhibits an inflammatory activity of C5a exerted on an inflammatory cell or tissue bearing a C5a receptor (C5aR).

9. The anti-inflammatory composition of claim 8, wherein said inflammatory activity of C5a inhibited by said peptide is selected from stimulation of chemotaxis, aggregation, degranulation, and production of superoxide anions in said C5aR-bearing inflammatory cell or tissue.

10. A method for inhibiting a C5a-mediated inflammatory response in a mammalian cell or mammalian subject, comprising administering to the mammalian cell or mammalian subject an anti-inflammatory effective amount of a peptide capable of binding C5a anaphylatoxin and inhibiting C5a activity, wherein the peptide comprises an amino acid sequence ASGAPAPGPAGPLRPMF (SEQ ID NO: 1), which method is effective to inhibit a C5a-mediated inflammatory response in said mammalian cell or subject.

11. The method of claim 10, wherein an N-terminal amino acid of said sequence is acetylated.

12. The method of claim 10, wherein said peptide inhibits an inflammatory activity of C5a exerted on an inflammatory cell or tissue bearing a C5a receptor (C5aR).

13. The method of claim 12, wherein said inflammatory activity of C5a inhibited by said peptide is selected from stimulation of chemotaxis, aggregation, degranulation, and production of superoxide anions in said C5aR-bearing inflammatory cell or tissue.

14. The anti-inflammatory composition of claim 6, wherein an amino terminal amino acid of said peptide is acetylated.

15. The peptide of claim 2, wherein said peptide inhibits an inflammatory signal or activity of C5a exerted on an inflammatory cell or tissue bearing a C5a receptor (C5aR).

* * * * *

SEQUENCE LISTING

```
<160> NUMBER OF SEQ ID NOS: 3

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ser Gly Ala Pro Ala Pro Gly Pro Ala Gly Pro Leu Arg Pro Met
  1               5                  10                  15

Phe

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ala Ala Arg Ile Ser Leu Gly Pro Arg Cys Ile Lys Ala Phe Thr
  1               5                  10                  15

Glu

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ser Thr Ala Pro Ala Arg Ala Gly Leu Pro Arg Leu Pro Lys Phe
  1               5                  10                  15

Phe
```